United States Patent [19]

Hermans

[11] 4,081,445
[45] Mar. 28, 1978

[54] CERTAIN BISPIPERAZIDO PHOSPHORUS COMPOUNDS

[75] Inventor: Johny C. Hermans, Wespelaar, Belgium

[73] Assignee: s.a. Texaco Belgium n.v., Brussels, Belgium

[21] Appl. No.: 628,288

[22] Filed: Nov. 3, 1975

[30] Foreign Application Priority Data

May 21, 1975 United Kingdom ............... 21796/75

[51] Int. Cl.² .................. C07D 295/16; C07D 295/22
[52] U.S. Cl. ................................ 260/268 K; 252/46.7; 252/49.9; 252/389 A; 544/121

[58] Field of Search ................... 260/268 K, 959, 958, 260/268 MK

[56] References Cited

U.S. PATENT DOCUMENTS

| 3,298,937 | 1/1967 | Strauss et al. | 260/959 |
| 3,531,550 | 9/1970 | Herber et al. | 260/959 |

*Primary Examiner*—R. Gallagher
*Attorney, Agent, or Firm*—Thomas H. Whaley; Carl G. Ries; Carl G. Seutter

[57] ABSTRACT

Compounds useful as lube oil additives are prepared by reaction of phosphorus halides and piperazine derivatives.

5 Claims, No Drawings

CERTAIN BISPIPERAZIDO PHOSPHORUS COMPOUNDS

FIELD OF THE INVENTION

This invention concerns bis-piperazido phosphorus and trispiperazido phosphorus compounds, and methods for the preparation of these compounds.

Various of the compounds obtained according to the invention are of interest as components of petroleum compositions, as additives for plastics materials, as components of flameresistant or flame-retardant polymers, as pharmaceuticals or as intermediates in the production of pharmaceuticals.

BACKGROUND OF THE INVENTION

It is known that halides of phosphorus are able to react with primary and secondary amines, thereby producing amides of the various acids or phosphorus. For instance, as long ago as 1898, Michaelis and Kaehner in Ber., 31 (1898), pp 1040–1047 described the reaction of piperidine and tetrahydroquinoline with phenyl phosphorus dichloride to form the corresponding bispiperidide and bis-tetrahydroquinolide. These compounds could be converted into the corresponding amides of phosphonic and phosphonothionic acid.

Subsequent work has described the reaction of phosphorus halides or oxyhalides with a variety of amines, and hydrazine. Attention is to be directed in this connection, for instance, to U.S. Pat. No. 2906770; 3107231; 3260702 and 3649594. Little attention, however, has been paid to the use of piperazine or substituted piperazines as amine reactants.

A paper by Bello et al in Macromolecules, 3 (1970) pp 98–100 describes the reaction of dimethylphosphoramidic dichloride $(CH_3)_2$-N-$POCl_2$ with an excess of piperazine to give phosphoric dimethylamido bispiperazide.

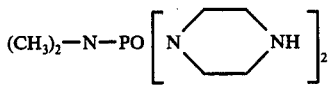

I

This compound was subsequently reacted with oxalyl dichloride or piperazine - 1,4 - dicarbonyl chloride to give polymers. Polymers with alternating piperazine and $(CH_3)_2N$-PO: groups were obtained by using an excess of the phosphorus halide.

The object of the present invention is the preparation of novel phosphorus compounds containing piperazine rings. Other objects of the invention are to produce novel phosphorus compounds useful as components of petroleum compositions. Further objects will be apparent to those skilled in the art.

STATEMENT OF THE INVENTION

The present invention provides compounds of the formula:

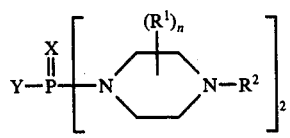

II and salts of such compounds, wherein

X represents an oxygen or sulphur atom or is absent,
Y represents an (i) aliphatic, cycloaliphatic, or aromatic hydrocarbon group or a heterocyclic group; (ii) a group of the formula $-NR_2$ in which each group R represents a hydrogen atom, an aliphatic, cycloaliphatic, or aromatic hydrocarbon group or a heterocyclic group, or the two groups R, together with the nitrogen atom to which they are attached, represent a N-containing heterocyclic ring; (iii) a group of the formula $-OR$ in which R has the meaning given above; or (iv) a group of the formula:

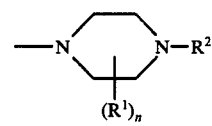

III $R^1$ represents a substituent on the piperazine ring;
$R^2$ represents a hydrogen atom or a substituted or unsubstituted aliphatic, cycloaliphatic or heterocyclic radical or heterocyclic group, an acyl group, a sulphonyl group a substituted phosphonyl group or a substituted carbamoyl group; and
n represents 0 or an integer, and salt of such compounds in which at least one of the groups $R^2$ represents a hydrogen atom;
but with the proviso that Y does not represent dimethylamino when X represents oxygen and $R^1$ and $R^2$ both represent hydrogen.

DESCRIPTION OF THE INVENTION

In the present invention the symbol X can represent an oxygen or sulphur atom, or it can be absent. The compounds according to the invention are therefore amides of phosphoric acid (when X represents oxygen), thiophosphoric acid (when X represents sulphur), and phosphorous acid (when X is absent).

The symbol Y can represent a group of the formula:

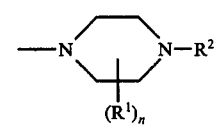

III in which case, the compounds of the invention are trispiperazides. When Y has one of its other meanings, the compounds are bispiperazides.

Y can for example represent a substituted or unsubstituted hydrocarbon group, which can be of aliphatic, cycloaliphatic or aromatic nature. Examples of suitable aliphatic groups are alkyl, such as methyl, ethyl, propyl, butyl, octyl, dodecyl, or octadecyl; alkenyl, such as allyl; or alkynyl, such as propargyl.

Examples of suitable cycloaliphatic groups are cycloalkyl, such as cyclohexyl, tetrahydronaphthyl or decahydronaphthyl; and cycloalkenyl, such as cyclohexenyl.

Examples of suitable aromatic hydrocarbon groups are aryl groups, such as phenyl, naphthyl, biphenyl, or phenanthryl; aralkyl, such as benzyl, or phenylethyl; and alkaryl, such as tolyl, dimethylphenyl, trimethylphenyl, cumyl, or p-octylphenyl.

Y can alternatively represent a heterocyclic group, linked to the phosphorus atom through a carbon atom, as in the tetrahydrofurfuryl or 2-pyridyl radicals.

Y can also represent a group of the formula $-NR_2$, in which each R represents a hydrogen atom, or an aliphatic, cycloaliphatic, or aromatic hydrocarbon group or a heterocyclic group. Examples of these hydrocarbon groups or heterocyclic groups are given above. Specific examples of suitable amino radicals are dimethylamino, diethylamino, dipropylamino, dibutyl amino, monomethyl amino, monoethylamino, monododecyl amino, mono-$(C_{10-14})$ alkylamino, monooctadecylamino, anilino, p-dodecylanilino, and N-butylanilino.

Alternatively, both symbols R, and the nitrogen atom to which they are attached, can together represent a heterocyclic radical linked to the phosophorus atom through the nitrogen atom. Examples of such groups are morpholino, piperidino, tetrahydroquinolino, pyrrolidino etc. The compounds in which Y represents a further piperazino group are, of course, a special instance of this.

Y can also represent a group of the formula —OR in which R has the meaning given above. Examples of such groups are alkoxy, such as methoxy, ethoxy, propoxy, butoxy, dodecyloxy and octadecyloxy; and aryloxy such as phenoxy, tolyloxy, or benzyloxy.

Any of the above radicals can if desired, be substituted. The only limitation upon the nature of the substituents is that they should be inert under the conditions of the reaction employed in synthesizing the compound.

In the group of the formula:

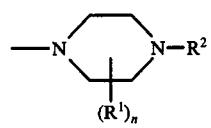

III $R^1$ represents a substituent on the piperazine ring. Here again, the only limitation upon the nature of the substituent is that it should be inert under the conditions of the reaction used to synthesize the compound. The substitutent can, for example, be one of the groups set out above for Y, provided that such a group is inert. When present, it can for example be an alkyl group, such as a methyl group. Alternatively, the substituent can have a meaning not set out above, insofar as it might not be an appropriate group for attachment to phosphorus; for example, an oxo group. Specific examples of substituted piperazine groups are 2,5-dimethylpiperazino and 2,5-dioxopiperazino groups, $n$ is 0 or an integer, and is preferably 0, 1 or 2:

$R^2$ can represent a hydrogn atom or a substituted or unsubstituted aliphatic, cycloaliphatic or aromatic hydrocarbon group or a heterocyclic group. Examples of suitable groups are set out above. Specifically preferred groups $R^2$ include alkyl, such as methyl, ethyl, phenyl, and substituted groups such as $\beta$-cyanoethyl and $\beta$-carbethoxy $R^2$ can also represent an acyl group, e.g. of an aliphtic, cycloaliphatic, aromatic or heterocyclic carboxylic acid, such as acetic, propionic, butyric or stearic acid, cyclohexane carboxylic acid, benzoic acid, toluic acid, nicotinic acid or a methylnicotinic acid. Alternatively $R^2$ can represent a sulphonyl group, for example a methane sulphonyl, benzene sulphonyl or toluene sulphonyl group.

$R^2$ can also represent a substituted phoshorus-containing group, e.g. a group of the formula $$-PXR_2^3$$

in which X has the meaning given above, and $R^3$ represents an aliphatic, cycloaliphatic or aromatic group, or a group of the formula —OR, —SR or $NR_2$ in which R has the meaning given above. An example of such a group is dimethylaminophosphonyl. $R^2$ can also represent a substituted carbamoyl group -CO-NHR wherein R has the meaning given above. An example of such a group is phenylcarbamoyl.

The invention also provides lubricating compositions comprising a major amount of a lubricating oil, and a minor amount (e.g. 0.1 to 10% by weight, preferably 0.5 to 2.5% by weight) of a piperazidophosphorus compound as defined above. The invention further provides a concentrate suitable for incorporating in a lubricating oil comprising a piperazidophosphorus compound as defined above and an inert diluent. The proportions of the diluent are not critical and the weight ratio of piperazidophosphorus compound to diluent may, for instance, range from 9:1 to 1:9 depending on miscibility.

Preferred lubricating compositions and concentrates comprise p-(p'-dodecylanilino) phenyl bispiperazido thiophosphate, and p-(p'-ethylanilino) phenyl bis-(N'-$\beta$-carbethoxyethylpiperazido) thiophosphate.

This invention also provides methods for the synthesis of the compounds described above. According to a preferred method, a compound of the formula:

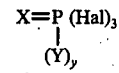

wherein y is an interger 0—1 (When y is 0, the compound has the formula iv; when y is 1, the compound has the formula v:

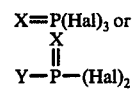   IV
   V in which X and Y have the meanings given above and Hal represents chlorine and bromine) is reacted with an excess of a piperazine derivative of the formula:

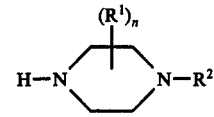

in which $R^1$, $R^2$ and $n$ have the meanings given above.

Compounds of the formula $X=P(Hal)_3$ and

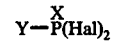

are well known in the art. Some of them will be commercially available, and others may be prepared by the methods described in, for example Houben-Weyl "Methoden der Organischen Chemie" Vol XII/2, or by Olah and Oswald in Ann. 625 (1959) 92–94.

Similarly, the piperazine derivatives will be well known in the art, and the preferred compound, piperazine itself, is commercially available. It is of course possible to employ a mixture of piperazine derivatives, thereby giving compounds in which the groups $R^1$ and/or $R^2$ on different piperazine rings are themselves different.

According to one preferred embodiment, the reaction according to the invention can be carried out by adding the phosphorus halide, as such or dissolved in an inert solvent, to a large excess of the piperazine, generally in a molar ratio of at least 1:4, either as such or dissolved in an inert solvent. Suitable solvents include, benzene, other hydrocarbons, ether or chloroform. The piperazine will act as both a catalyst and a halogen acid-acceptor.

The reaction is exothermic and can be moderated by controlling the rate at which the phosphorus halide is added. The reaction can generally be carried out at room temperature, but it is possible to carry it out at elevated temperature, e.g. at a temperature of 60° to 80° C. in benzene, toluene or xylene or at the reflux temperature of the solvent employed. Most conveniently the reaction is carried out at atmospheric pressure, but superatmospheric pressures can be employed if desired. The piperazine hydrohalide that forms is insoluble in many solvents, e.g. ether, benzene, and other hydrocarbons, and can be separated by filtration. It can also be removed by washing with water or an aqueous solution of sodium carbonate. Subsequently, any solvent and any excess of the piperazine can be distilled off, and the resulting crude product can be purified by recrystallization, low-pressure distillation or a chromatographic technique.

Alternatively, the reaction can be carried out in the presence of a tertiary amine as catalyst and hydrogen halideacceptor. Examples of a suitable tertiary amines are triethylamine, pyridine, dimethylaniline and lutidine. The tertiary amine can be present in either or both of the phosphorus halide and the piperazine. It is most convenient however to use piperazine as catalyst and hydrogen halide-acceptor as the reaction course is more easily followed.

At least stoichiometric amounts of piperazine, corresponding to the phosphorus halide, are required in this embodiment of the invention, and advantageously an excess of the piperazine is employed. The molar ratio of phosphorus halide: piperazine: tertiary amine, can be, or example 1:2:2.

When $R^2$ in the piperazine reactant is hydrogen, for instance in piperazine itself, the product of the synthetic reaction will have the structure:

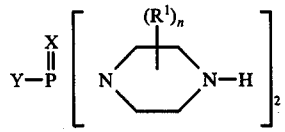

VII and wil itself be capable of undergoing further reactions. For instance, the N-H group can be subjected to a substitution reaction with a compound of the formula $R^2$ - Hal, for instance an acyl, phosphonyl or sulphonyl halide such as acetyl chloride, benzoyl chloride, phenyl dimethylaminophosphonyl chloride, benzene sulphonyl chloride or toluene sulphonyl chloride.

Alternatively the compound of formula VII can be reacted with an acrylic compound of the formula:

$$CH_2=CH-Z \quad \quad VIII$$

wherein Z represents a cyano, carboalkoxy, sulphone ($SO_2R$) or phosphonyl ($PX R_2$) group, e.g. with acrylonitrile or an ester of acrylic acid. The products have the formula II in which $R^2$ represents a group of the formula $-CH_2-CH_2-Z$.

Yet another reaction which can be undergone by compounds of the formula VII is reaction with an isocyanate of the formula R-NCO wherein R has the meaning given above. The products of this reaction are substituted ureas of the formula II in which $R^2$ represents a group of the formula:

$$-CO-NH-R \quad \quad IX$$

Examples of suitable isocyanates are methylisocyanate and phenyl isocyanate.

The compounds according to the invention have a variety of uses. They constitute multifunctional lubricating oil additives, exhibiting an anti-corrosionoxidation action and an anti-wear action, and are mild extreme pressure agents. Since the compounds in which $R^2$ represents hydrogen are difunctional and trifunctional secondary amines, they are able to participate in polymer-forming and cross-linking by polyaddition and polycondensation reactions. The compounds in which $R^2$ for example represents a $\beta$-carboalkoxyethyl group constitute flame-retardant plasticizers. Other actual and potential uses will be apparent to those skilled in the art.

DESCRIPTION OF SPECIFIC EMBODIMENTS

Practice of this invention will be apparent to those skilled in the art from inspection of the following illustrative examples.

EXAMPLE 1

0.20 mole of phenyldichlorophosphate dissolved in 50 ml of benzene was added dropwise to a mixture of 4.0 mole of piperazine and 0.50 mole of triethylamine dissolved in 800 ml of benzene at 50–80° C. The mixture was mechanically stirred. When all the acid chloride was added, the mixture was refluxed for one to two hours and the precipitated triethylamine hydrochloride was filtered off. The filtrate was cooled, and more precipitated hydrochloride was filtered off. The solvent and the excess of piperazine were distilled off at normal pressure. 250 g. of piperazine were recovered. The remaining piperazine was removed under vacuum at 60°–90° C and a crude product was obtained, which could be crystallized from benzene from acetone or from a mixture of both, yielding colourless white crystals of phenylbispiperazidophosphate mp, II4.5° – II5° C. The crude product can also be purified by vacuum distillation b.p. 235°/0.4mm. The total yield was more than 60% of the theoretical amount.

A standard procedure used for the synthesis of bis-piperazido compounds is as follows:

To 1 mole of anhydrous piperazine dissolved in 600 ml of dry benzene at 50°–80° C is slowly added 0.10 mole of the phosphorus acid dichloride (Y-PXCl$_2$; X=O, S or absent) dissolved in 50 to 100 ml of benzene, while the mixture is gently stirred. The mixture is then refluxed for 15 to 30 minutes and the precipitated piperazine hydrochloride is filtered off. Benzene and the excess of piperazine are distilled off at reduced pressure (up to 80–100° C at 1 mm). This process easily occurs on a thin film rotating evaporator. The residue is redissolved in benzene (400 ml) and the remaining piperazine hydrochloride is filtered off. Benzene and the remaining piperazine are then distilled off under vacuum (up to 100° C at 0.5–1 mm) which yields the crude piperazidophosphorus compound.

Sometimes toluene or xylene was used as a solvent to provide a higher reaction temperature, needed to complete the reaction (e.g. for bispiperazidophosphoric triamides), which also had the advantage that it prevented blocking of the condensor by sublimed piperazine when it was distilled off. Purification of the crude products was sometimes possible by recrystallization or by distillation, but most compounds decomposed upon distillation; several were viscous oils which sometimes solidified on standing.

For this preparation usually piperazine itself was used as HCl-acceptor because the use of other bases e.g. triethylamine gave no advantages. In contrast, using triethylamine, it was not possible to determine the extent of conversion on the basis of the amount of salt formed, because a mixture of triethylamine hydrochloride and piperazine hydrochloride precipitated during the reaction.

A variant of the work-up method consists in washing out the piperazine hydrochloride and piperazine from the reaction mixture with water or dilute sodium carbonate solution, directly after the reaction or preferably after the removal of the main part of piperazine and/or its salt. This procedure is not suitable for piperazidophosphorus compounds which have good solubility in water, and hence it is recommended to extract such phosphorus compounds from the wash waters, for example with chloroform, to avoid extensive losses of the reaction product.

Typical examples of compounds prepared by the standard procedure are:

EXAMPLE 2

Phenyl bispiperazidophosphate

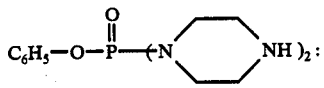

0.5 mole (105.5 g) of $C_6H_5$—O—$POCl_2$ was reacted with 5 mole (430 g) of piperazine dissolved in 3 l of benzene. The standard work up procedure, including filtration of the hydrochloride and distillation of the solvent and excess piperazine, yielded 143 g (92%) of a crude product which was first recrystallized from benzene (yield: 115.5 g; 74.3%) and then from benzene: acetone (1:1) which yielded 92.2 g (59.9%) with mp 117°–118° C. From the remaining viscous oil another fraction of pure compound could be isolated by vacuum distillation (bp 235° C/0.4 mm). Other compounds, indicated in Table 1 below, were prepared by similar methods.

TABLE 1

Bispiperazidophosphoryl Compounds

| Compound Y= | Yield % | Melting Point (° C) |
|---|---|---|
| —O—$C_2H_5$ | 100 | oil |
| —O—$(CH_2)_{17}$—$CH_3$ | 86.4 | 66.5–68.5 |
| —O—$C_6H_5$ | 74.3 | 117–118 |

TABLE 1-continued

Bispiperazidophosphoryl Compounds

| Compound Y= | Yield % | Melting Point (° C) |
|---|---|---|
| —NH($CH_2)_{17}$—$CH_3$ | 95 | 46–47 |
| —NH—[$C_{10}$–$C_{14}$] | 82.7 | oil |
| —N($C_3H_7)_2$ | 100 | oil |
| —N(morpholino) | 82 | 125 |
| —NH—$C_6H_5$ | 56 | 155–157 |
| —NH—$C_6H_4C_{12}H_{25}$ | 88.8 | glassy solid |

EXAMPLE 3

Ethyl bispiperazidothiophosphate:

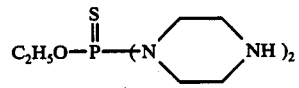

(a) 0.1 mole (17.9 g) of ethyl thiophosphoryl dichloride ($C_2H_5O$—$PSCl_2$) was reacted with 1 mole (86 g) of piperazine dissolved in 600 ml of benzene at 70° C. Standard work up (with a maximum temperature of 70° C) yielded a crude yellow oil (27.45 g; 98.5%, mp 84°–95° C) which solidified on standing and which was recrystallized from ether:acetone (4:1) yielding yellow-white crystals with mp 96°–101° C.

(b) 0.0625 mole (11.2 g) of ethyl thiophosphoryl dichloride was reacted at 40° C with 0.45 mole (39.4 g) of piperazine dissolved in benzene. After removal of the salt, benzene solution was extracted four times with water. The benzene solution was dried and concentrated (T < 40° C) yielding an oil $F_1$ (2.2 g; 12.6%). The collected wash water was extracted three times with chloroform which yielded, after evaporation of the solvent, an oil $F_2$ (13.7 g; 78.7%; mp 78.5°–81.5° C) which crystallized out on standing. Overall yield: 15.9 g (91.4%). Elemental analysis of $F_2$ was correct. Other compounds, indicated in Table 2 below, were prepared by similar methods.

TABLE 2

Bispiperazidothiophosphoryl Compounds

| Compound Y= | Yield % | Appearance Melting range ° C[b] |
|---|---|---|
| —O—$CH_2$—$CH_3$ | 91.4 | Yellow oil (78.5–81.5) |
| —O—$C_6H_5$ | 96 | Yellow oil (56 – 63) |
| —O—$C_6H_4$—NH—$C_6H_4$—$C_2H_5$ | 94 | Red Oil |
| —O—$C_6H_4$—NH—$C_6H_4$—$C_{12}H_{25}$ | 98.5 | Brown Oil |
| —N($CH_2$—$CH_2$—$CH_2$—$CH_3)_2$ | 53.7 | Yellow oil (85 – 92) |
| —N($C_6H_5)(C_4H_9)$ | 88.6 | Brown oil |
| —O—$(CH_2)_{17}$—$CH_3$[a] | 93.2 | Waxy solid (45 – 50) |

[a]No good elemental analysis was obtained of this compound
[b]Melting range of the solidified oil

EXAMPLE 4

Phosphorous Di-n-butylamido bispiperazide

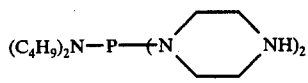

To 0.93 mole (80.10 g) of piperazine dissolved in 1.5 l of benzene at 45° C was added slowly 0.07 mole (16.1 g) of Bu$_2$NPCl$_2$ in 100 ml of benzene. Then the mixture was warmed up till reflux, filtered, and benzene and the excess of piperazine were removed under reduced pressure (T$_{max}$: 100° C). The crude product obtained was redissolved in benzene, filtered again and the mixture was concentrated, which yielded 19.4 g (84.12%) of the bispiperazidophosphorous compound.

Table 3 below indicates this compound, and the corresponding phenoxy compound, prepared in similar manner.

TABLE 3

Bispiperazidophosphorus (P$^{III}$) Compounds

HN⟨N—P—N⟩NH
     |
     Y

| Compound Y= | Yield % | Appearance |
|---|---|---|
| C$_6$H$_5$—O— | 82.3 | viscous oil |
| (C$_4$H$_9$)$_2$N— | 84.1 | viscous oil |

EXAMPLE 5

Phenyl bis (N'-β-cyanoethylpiperazido) phosphate

0.025 mole (7.75 g) of phenyl bispiperazidophosphate was refluxed with 0.075 mole of (5 ml) acrylonitrile in 50 ml of toluene (6–7 hrs). After stripping off the solvent and the excess acrylonitrile, a crude oil was obtained (10.2 g; 97.8%). Purification by vacuum distillation resulted in decomposition of the product (250° C/0.6 mm), which however can be purified by column chromatography on silica gel (eluting with methanol) yielding a yellow-red viscous oil.

EXAMPLE 6 p-(p'-ethylanilino)phenyl -bis(N'carbethoxyethyl-piperazido) thiophosphate.

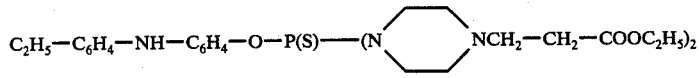

A solution of 6.7 g (0.015 mole) of p-(p'-ethylanilino) phenyl-bis-piperazido thiophosphate and 5 g (0.05 mole) of ethyl acrylate in 100 ml of toluene was refluxed for 4–6 hrs. Then toluene and the excess ethyl acrylate were stripped off under vacuum (temp. max. 100° C) which yielded the title compound, a viscous brown oil, in 96% yield (9.3 g).

EXAMPLE 7

Phosphorous dibutylamido bis-(N'-carbanilidopiperazide)

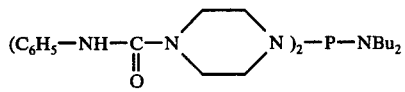

To 0.005 mole (1.647 g) of phosphorousdibutylamido bispiperazide in 30 ml of benzene at 20° C was slowly added 0.010 mole (1.19 g) of phenyl isocyanate in 20 ml of benzene. Immediately a white precipitate was formed which could be partly recrystallized from boiling ethanol. Yield of the title compound: 1.8 g; 63.5%, mp 320° C.

EXAMPLE 8

Phosphoric trispiperazide

To 1 mole (86 g) of anhydrous piperazine dissolved in 600 ml of dry benzene at 50°–60° C was added dropwise with gentle stirring 0.05 mole (7.66 g) of POCl$_3$ dissolved in 50 ml of dry benzene. The mixture was refluxed for 2 hrs at 80° C and then filtered hot to remove precipitated piperazine hydrochloride. Benzene and the excess of piperazine were distilled off at reduced pressure (up to 80°–100° C at 1 mm). The residue was redissolved in dry benzene, filtered to remove remaining salt, and again benzene and piperazine were distilled off under reduced pressure.

A crude product was obtained in a yield of 13.7 g (90.7%), melting point 130° C. Once it had absorbed water, the compound could not be redissolved and recrystallized from benzene and it became very sticky. Pure product could be obtained again from it, by dissolving it in alcohol (ethanol) and distilling off all the solvents under vacuum (80°–100° C/1 mm). A pale yellowish oil was obtained which crystallized out upon cooling and standing, and which gave a good elemental analysis. Yield 9 g (59.6%).

EXAMPLE 9

Thiophosphoric trispiperazide

To 1 mole (86 g) of anhydrous piperazine dissolved in 200 ml of toluene at 100° C was added dropwise with gentle stirring 0.05 mole (8.47 g) of PSCl$_3$ in 30 ml of toluene. The mixture was refluxed for 21 hrs and the precipitated piperazine hydrochloride was filtered off. Toluene and the excess of piperazine were distilled off at reduced pressure (100° C/1 mm).

15 g of a crude solid were obtained and recrystallized from toluene/benzene yielding pale yellow crystals 13.1 g (86.7%) mp 129.5°–130.5° C and which gave a good analysis. This compound was fairly hygroscopic, and had good solubility in water and alcohol, but it was not soluble in base oils.

EXAMPLE 10

Thiophosphoric tris-(N'-βcyanoethylpiperazide)

A solution of 0.02 mole (6.37 g) of phosphorothioic trispiperazide and 0.09 mole (4.77 g) of acrylonitrile in 110 ml benzene was refluxed for 6 hrs. Stripping off the solvent and excess acrylonitrile (temp max 100° C/10 mm) yielded a crude yellow oil 9.5 g (99%) which was purified by column chromatography over silica gel using methanol as eluent. Pure white crystals of thiophosphoric tris-(N'-β-cyanoethylpiperazide) were obtained (7.83 g; 82%); mp 122° C). The solubility in base oils of this compound was very low.

EXAMPLE 11

Thiophosphoric tris-(N'-β-carbethoxyethylpiperazide)

(a) A mixture of 0.010 mole (3.18 g) phosphorothioic trispiperazide and 0.030 mole (3.0 g) of ethyl acrylate was heated under reflux for 5 hrs at 140° C. After the excess of ethyl acrylate was distilled off, a brown oil was obtained in 99.5% yield (6.15 g) which gave a good analysis.

(b) A mixture of 0.0104 mole (3.30 g) of phosphorothioic trispiperazide and 0.20 mole (20 g) of ethyl acrylate in 100 ml toluene was refluxed for 4 hrs. The solvent and excess ethyl acrylate was stripped off which yielded the compound in 96.6% (6.2 g) yield.

pounds in which X=S and Y=O-alkyl groups and with compounds in which X=S and in which $R^2$=carboxylic ester (—$CH_2$—$CH_2$—COOR). All these compounds show mild extreme pressure activity and the diarylaminophosphorus compounds (Y=—O—$C_6H_4$—NH—$C_6H_4$—R) are excellent oxidation inhibitors, superior to ZDT. Bench test results of the trivalent phosphorus compound, phenyl bispiperazidophosphite showed moderate anti-wear and anti-oxidation action and mild extreme pressure properties.

According to the test results the most promising compounds prepared are p-(p'-dodecylanilino)phenyl bis-piperazidothiophosphate

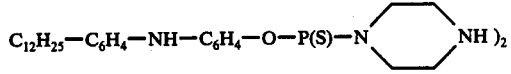

and derivatives of the arylaminophenylbispiperazidothiophosphates

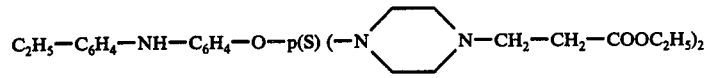

EXAMPLE 12

Only the piperazidophosphorus compounds and derivatives which had a solubility in base oils (SNO-20; 145-PPT) of at least 0.5% wt were evaluated as lube oil additives. The results are listed in Tables 4, 5, 6 and 7 below, and indicate that the bispiperazidophosphoryl compounds show a moderate wear protection and mild extreme pressure properties compared to ZDT, (a zinc dialkyl dithiophosphate), and cause no copper corrosion and slight to moderate rusting.

The general performance of the thiophosphoryl compounds was better than of the phosphoryl compounds. Compared to ZDT, their wear protecting action is good to excellent, the best results being obtained with compounds which give a very good wear protection, an excellent oxidation inhibition and mild extreme pressure activity.

The hydrocarbon base oils designated SNO-20 and 145-PPT have the following properties:

|  | SNO-20 | 145-PPT |
| --- | --- | --- |
| Sp Gr 60/60F | 0.871-.887 | 0.860-.876 |
| Gravity API | 28-31 | 30-33 |
| Vis, SUS at 100° F | 325-350 | 140-150 |
| Vis, SUS at 210° F | 53-55 | — |
| VI | 90 min. | 95 min. |
| Pour Point ° F | 10 | 10 |

TABLE 4

Evaluation of Bispiperazidophosphoryl Compounds

| Compound | Blend wt % in | Cu-Strip corrosion[1] | Rust[2] | 4 Ball Navy Wear[3] micr/min | Mean Hertz Load[4] kg | Weld Point[4] kg | Rotary Bomb Oxidation[5] min |
| --- | --- | --- | --- | --- | --- | --- | --- |
| HN⟨piperazine⟩N—P(=O)(—N(C₃H₇)₂)—N⟨piperazine⟩NH | 1.0 SNO-20 DTA | 1A | slight | 4.6 | 53.3 | 158 | 20 |
| HN⟨piperazine⟩N—P(=O)(—NH(C₁₀–C₁₄))—N⟨piperazine⟩NH | 0.75 SNO-20 DTA | 1A | moderate | 4.1 | 53.9 | 158 | 40 |
| ZDT | 0.5 SNO-20 DTA | | | — | 48 | 224 | — |
|  | 1.0 SNO-20 DTA | 1A | moderate | 0.3 | 54.9 | 200 | 65 |
| SNO-20 DTA | — | 1A | severe | 7.3 | 24 | 126 | 40 |

[1]ASTM-D130, 3 hr, 212°0 F
[2]ASTM-D665A, 60° C, 24 hr
[3]ASTM-D 2266-64, 1800 rpm. 28 kg, room temp.
[4]ASTM-D2596, 1500 rpm. room temp.
[5]ASTM-2272, 100 rpm. 90 psi, 150° C

TABLE 5
Evaluation of Piperazidothiophosphoryl Compounds

Compound $$Y-\overset{S}{\underset{\|}{P}}-(N\bigcirc NH)_2$$

| Y = | Blend wt % in Base oil | Cu-strip corrosion[1] | Rust[2] | 4 Ball Navy-Wear[3] micr/min | Mean Hertz Load[4] kg | Weld Point[4] kg | Rotary Bomb Oxidation[5] min |
|---|---|---|---|---|---|---|---|
| $-O-C_2H_5$ | 1.0 SNO-20 DTA | 1A | pass | 1.9 | 54.6 | 158 | 20 |
| $-O-(CH_2)_{17}-CH_3$ [a] | 1.0 SNO-20 DTA | 1A | slight | 0.5 | 43.2 | 158 | 35 |
| $-O-C_6H_5$ | 1.0 SNO-20 DTA | 1A | pass | 2.4 | 53.2 | 158 | 40 |
|  | 2.0 145-PPT | 1B | pass | 2.6 | 43.2 | 158 | 30 |
| $-N(C_6H_5)(C_4H_9)$ | 1.0 SNO-20 DTA | 1A | pass | 1.4 | 54.2 | 158 | 108 |
| $-O-C_6H_4-NH-C_6H_4-C_{12}H_{25}$ | 0.47 SNO-20 DTA | 1B | very slight | 1.1 | 29.1 | 158 | 508 |

Compound $$Y-\overset{S}{\underset{\|}{P}}(N\bigcirc N-(CH_2)_2COOC_2H_5)_2$$

| Y = | Blend wt % in Base oil | Cu-strip corrosion[1] | Rust[2] | 4 Ball Navy-Wear[3] micr/min | Mean Hertz Load[4] kg | Weld Point[4] kg | Rotary Bomb Oxidation[5] min |
|---|---|---|---|---|---|---|---|
| $-O-C_6H_4-NH-C_6H_4-C_2H_5$ | 0.5 SNO-20 DTA | 1A | no rust, deposit | 0.3 | 29 | 158 | 220 |
| $-N\bigcirc N-(CH_2)_2-COOC_2H_5$ | 0.6 SNO-20-DTA | 1A | severe | 0.5 | 43.3 | 158 | 30 |

References

| | Blend wt % in Base oil | Cu-strip corrosion[1] | Rust[2] | 4 Ball Navy-Wear[3] micr/min | Mean Hertz Load[4] kg | Weld Point[4] kg | Rotary Bomb Oxidation[5] min |
|---|---|---|---|---|---|---|---|
| ZDT | 0.5 SNO-20-DTA | | | | 48 | 224 | |
| | 1.0 SNO-20-DTA | 1A | moderate | 0.3 | 54.9 | 200 | 65 |
| | 2.0 145 PPT | 1A | severe | 2.6 | 67.4 | 200 | 210 |
| SNO-20-DTA | — | 1A | severe | 7.3 | 24 | 126 | 40 |
| 145 PPT | — | | | 6.6 | 23 | 126 | 20 |

[1] ASTM-D130, 3 hr, 212° F.
[2] ASTM-D665A, 60° C. 24 hr.
[3] ASTM-D2266-64, 1800 rpm 28 kg, room temp.
[4] ASTM-D2596, 1500 rpm, room temp.
[5] ASTM-2272, 100 rpm, 90 psi 150° C.
[a] The reaction product of $C_{18}H_{37}OPSCl_2$ and piperazine, but with uncertain structure

TABLE 6
Evaluation of Phenyl Bispiperazidophosphite

| Compound | Blend % wt in Base oil | Cu-strip Corrosion[1] | Rust[2] | 4 Ball Navy Wear micr/min | Mean Hertz Load[4] kg | Weld Point[4] kg | Rotary Bomb Oxidation[5] min |
|---|---|---|---|---|---|---|---|
| $C_6H_5-O-P(N\bigcirc NH)_2$ | 2.0 SNO-20 | 1A | pass | 1.8 | 54.7 | 158 | 70 |
| ZDT | 2.0 SNO-20 | — | — | 0.2 | 62 | 251 | 120 |
| SNO-20 | — | 1A | severe | 7.3 | 24 | 126 | 40 |

[1] ASTM-D130, 3 hr, 212° F
[2] ASTM-D665A, 60° C, 24 hr.
[3] ASTM-D2266-64, 1800 rpm. 28 kg, room temp.
[4] ASTM-D2596, 1500 rpm room temp.
[5] ASTM-2272, 100 rpm. 90 psi, 150° C.

The solubility in base oils at room temperature of phosphorothioic tris-(N'-β-carbethoxyethylpiperazide) is 0.6% wt in SNO-20 and 0.3% wt in 145-PPT, allowing an evaluation as lube oil additive.

The compound has good antiwear properties and mild extreme pressure activity, compared to ZDT a zinc dialkyl dithiophosphate.

Test data are given in Table 7 below:

TABLE 7

| Bench Test | Phosphorothioic tris-(N'-β-carbethoxy ethylpiperazide) | SNO-20 | ZDT 0.5 wt. % | in SNO-20 1 wt. % |
|---|---|---|---|---|
| Cu strip corrosion ASTM-D130; 3 hr; 212° F | 1A | 1A | — | 1A |
| Rust ASTM-D665A 60° C, 24 hr | severe | severe | — | moderate |
| 4 ball Navy Wear ASTM-D2266-64 1800 rpm 28 kg, room temp | 0.5 micr/min | 7.3 micr/min | — | 0.3 micr/min |

TABLE 7-continued

| Bench Test | Phosphorothioic tris-(N'-β-carbethoxy ethylpiperazide) | SNO-20 | ZDT in SNO-20 0.5 wt. % | 1 wt. % |
|---|---|---|---|---|
| Mean Hertz Load ASTM-D2596 1500 rpm, room temp | 43.3 kg | 24 kg | 48 kg | 54.9 kg |
| Weld Point ASTM-D2596 1500 rpm, room temp | 158 kg | 126 kg | 224 kg | 200 kg |
| Rotary bomb oxidation ASTM 2272, 100 rpm, 90 psi, 150° C | 30 min | 40 min | — | 65 min |

Although this invention has been illustrated by reference to specific embodiments, it will be apparent to those skilled in the art that various changes and modifications may be made which clearly fall within the scope of this invention.

What we claim is:

1.

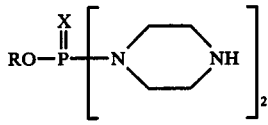

wherein

X represents an oxygen or sulfur atom or is absent; and

R represents a hydrogen atom, a $C_1$-$C_{18}$ alkyl group, or a phenyl group.

2. A compound selected from the group consisting of
Ethyl bispiperazidophosphate;
n-Octadecyl bispiperazidophosphate;
Phenyl bispiperazidophosphate;
Ethyl bispiperazidothiophosphate
Phenyl bispiperazidothiophoshate;
Octadecyl bispiperazidothiophosphate; and
Ethyl bispiperazidophophite.

3. Phenyl bispiperazidophosphate.

4. Ethyl bispiperazidophosphate.

5. Octadecyl bispiperazidophosphate.

* * * * *

UNITED STATES PATENT AND TRADEMARK OFFICE
CERTIFICATE OF CORRECTION

PATENT NO. : 4,081,445

DATED : March 28, 1978

INVENTOR(S) : Johny C. Hermans

It is certified that error appears in the above-identified patent and that said Letters Patent are hereby corrected as shown below:

Col. 16, line 27, correct the spelling of

-- bispiperazidophosphite --.

Signed and Sealed this

Twenty-third Day of October 1979

[SEAL]

Attest:

RUTH C. MASON
Attesting Officer

LUTRELLE F. PARKER
Acting Commissioner of Patents and Trademarks